United States Patent
Gabel et al.

(10) Patent No.: US 6,689,755 B1
(45) Date of Patent: Feb. 10, 2004

(54) METHOD OF STABILIZING BIOLOGICALLY ACTIVE SUBSTANCES

(75) Inventors: Rolf-Dieter Gabel, Schwetzingen (DE); Markus Mattern, Heppenheim (DE); Gerhard Winter, Dossenheim (DE); Alexander Wirl, Heuchelheim (DE); Heinrich Woog, Laudenbach (DE)

(73) Assignee: Boehringer Mannheim GmbH, Mannheim (DE)

( * ) Notice: Subject to any disclaimer, the term of this patent is extended or adjusted under 35 U.S.C. 154(b) by 0 days.

(21) Appl. No.: 09/184,866

(22) Filed: Nov. 3, 1998

(30) Foreign Application Priority Data

Nov. 3, 1997 (EP) .............................. 97119112

(51) Int. Cl.$^7$ ........................ C08B 30/00; A01N 43/04; A61K 31/70
(52) U.S. Cl. ........................ 514/23; 127/34; 514/911; 514/970; 530/350; 530/351; 530/397; 530/399; 530/354; 424/489; 424/85.1; 424/85.2; 424/94.1; 424/94.3; 424/94.6; 424/499; 424/500; 435/810
(58) Field of Search ............................ 127/34; 514/23, 514/911, 970; 530/350, 351, 397, 399, 354; 424/489, 85.1, 85.2, 94.1, 94.3, 94.6, 499, 500; 435/810

(56) References Cited

U.S. PATENT DOCUMENTS

| | | | |
|---|---|---|---|
| 3,281,216 A | * 10/1966 | Mindick et al. ............... 23/299 |
| 3,330,749 A | * 7/1967 | Kuwata et al. |
| 3,882,228 A | 5/1975 | Boneey et al. ................. 424/35 |
| 4,734,401 A | 3/1988 | Blouin |
| 4,824,938 A | 4/1989 | Koyama et al. ............. 530/351 |
| 5,290,765 A | 3/1994 | Wettlaufer et al. ............ 514/23 |
| 5,356,636 A | 10/1994 | Schneider et al. ........... 424/489 |
| 5,763,409 A | 6/1998 | Bayol et al. ................... 514/21 |
| 5,955,448 A | * 9/1999 | Colaco et al. ................. 514/53 |
| 2001/0055617 A1 | * 12/2001 | Mattern et al. ............. 424/489 |

FOREIGN PATENT DOCUMENTS

| | | |
|---|---|---|
| AU | 2 853 989 | 7/1989 |
| CA | 2235243 | 4/1998 |
| DE | 2 058 434 | 6/1971 |
| EP | 325 112 | 7/1989 |
| EP | 383 569 | 2/1990 |
| EP | 229 810 | 10/1991 |
| EP | 520 748 | 12/1992 |
| EP | 682 944 | 5/1995 |
| WO | 91 18091 | 11/1991 |
| WO | 96 32096 | 10/1996 |
| WO | 97 15288 | 5/1997 |

OTHER PUBLICATIONS

Teck–Yeo Ting et al, Microparticles of Polyvinyl Alcohol for Nasal Delivery. I. Generation by Spray–Drying and Spray–Desolvation, Pharmaceutical Research, Oct. 1992, vol. 9, No. 10, pp. 1330–1335.

F. Pavenetto et al, Evaluation of spray drying as a method for polylactide and polylactide–co–glycolide microsphere preparation, J. Microencapsulation, Oct.–Dec. 1993, vol. 10, No. 4, pp. 487–497.

John Berriman et al, Analysis of transient structures by cryo–microscopy combined with rapid mixing of spray droplets, Ultramicroscopy, Dec. 1994, vol. 56, No. 4, pp. 241–252.

Shun Por Li et al, Development and in Vitro–in Vivo Evaluation of a Multiparticulate Sustained Release Formulation of Diltiazem, Pharmaceutical Research, Sep. 1995, vol. 12, No. 9, pp. 1338–1342.

Chrysantha Freitas et al, Spray–Drying of solid lipid nano-particles (SLN™), European Journal of Pharmaceutics and Biopharmaceutics, Sep. 1998, vol. 46, No. 2, pp. 145–151.

Rudolf Voight, 7$^{th}$ Edition, ISBN 3–8126–013–1, Chapter 2.2.3.2.2 ("Spruhtrocknung") (1993).

K. Tanaka, T. Takeda & K. Miyajima, Chem. Pharm. Bull., 39, pp 1091–1094, 1991.

F. Franks, Cyro–Letters, 11, pp 93–110, 1990.

M. J. Pikal, BioPharm. 3, pp. 26–30, 1990.

F. Franks, Jap. J. Freezing & Drying, 38, pp. 5–16, 1992.

J. F. Carpenter & J. H. Crowe, Crybiol., 25, pp. 459–470, 1988.

F. Franks & R. H. M. Hatley, Stability & Stabilization of Enzymes, Elsevier Sci. Publ., pp. 45–54, 1993.

J. F. Carpenter & J. H. Crowe, Biochemistry, 28, pp. 3916–3922, 1989.

B. Roser, BioPharm, 4, pp. 47–53, 1991.

T. Arakawa, Y. Kita & J. F. Carpenter, Pharm. Res., 8, pp 285–291, 1991.

* cited by examiner

*Primary Examiner*—Mary K. Zeman
(74) *Attorney, Agent, or Firm*—George W. Johnston; Patricia S. Rocha-Tramaloni; Kimberly J. Prior

(57) ABSTRACT

The present invention relates to a rapid and readily reproducible process for stabilizing biologically active substances by combining the biologically active substance witha a stabilizingmixture and drying the resulting mixture into a dry, amorphous product by means of convection drying. The invention also relates to the amorphous, microscopically homogeneous products which are obtained by this process, are in the form of powders and have a uniform geometric, in particular spherical, shape. The invention furthermore relates to the use of substance mixtures for stabilizing biologically active material, in particular proteins by means of spray drying.

8 Claims, No Drawings

METHOD OF STABILIZING BIOLOGICALLY ACTIVE SUBSTANCES

The present invention relates to a rapid and readily reproducible process for stabilizing biologically active substances by combining the biologically active substance with a stabilizing mixture and drying the resulting mixture into a dry, amorphous product by means of convection drying. The invention also relates to the amorphous, microscopically homogeneous products which are obtained by this process, are in the form of powders and have a uniform geometric, in particular spherical, shape. The invention furthermore relates to the use of substance mixtures for stabilizing biologically active material, in particular proteins by means of spray drying.

BACKGROUND OF THE INVENTION

It is well known that proteins, especially human proteins, can be stabilized in solid preparations by a large number of substances, preferably by sugars or combinations of sugars and amino acids.

Various processes and formulations for producing dry, biologically or therapeutically active materials are described. By dry materials are meant substances and substance mixtures which have a residual moisture content not exceeding 8% (g/g), preferably not exceeding 4% (g/g), particularly preferably not exceeding 2%. Freeze-drying processes are widely used for producing such formulations [F. Franks, Cryo Lett. 11, 93–110, (1990); M. J. Pikal, Biopharm. 3 (9), 26–30 (1990); M. Ilora, Pharm. Research 8 (3), 285–291 (1992); F. Franks, Jap. J. Freezing Drying 38, 15–16, (1992)] but have the specific disadvantages of freeze-drying. They consume large amounts of energy, require the use of refrigerants, some of which are environmentally harmful (frigens), and are time-consuming because it is often necessary to remove relatively large volumes of ice by sublimation. The freezing step necessary for freeze-drying may be destabilizing for a large number of substances, especially for proteins. This process is therefore not applicable at all to some biological materials.

Alternatives to freeze drying for producing dry protein preparations are processes which dry the material by using heat and/or vacuum [F. Franks, R. M. H. Hatley: Stability and Stabilization of Enzymes; Eds. W. J. J. von den Teel, A. Harder, R. M. Butlaar, Elsevier Sci. Publ. 1993, pp. 45–54; B. Roser, Biopharm, 4 (9), 47–53 (1991); J. F. Carpenter, J. H. Crowe, Cryobiol. 25, 459–470 (1988)]. Examples which may be mentioned in this connection are vacuum drying with or without use of elevated temperature, spray-drying processes in a wide variety of modifications, including combined use of vacuum and spraying techniques, and drum drying and other thin-film drying processes.

J. F. Carpenter, J. H. Crowe, Biochemistry 28, 3916–3922 (1989); K. Tanaka, T. Taluda, K. Miyajima, Chem. Pharm. Bull. 39 (5), 10–94 (1991), DE 35 20 228, EP 0 229 810, WO 91/18091, EP 0 383 569 and U.S. Pat No. 5,290,765 describe preparations which contain sugars or sugar-like substances. However, the production of dry, carbohydrate-containing preparations by means of freeze or vacuum drying, especially of sugar preparations, is associated with disadvantages in the state of the art. These include, inter alia, high energy consumption for drying to an acceptable residual moisture content, extended process times at low drying temperatures, formation of highly viscous, water-containing masses (called "rubber") or glassy melts whose glass transition temperatures are below room temperature. The disadvantages described above significantly influence the stability of biological materials in such preparations.

It is also evident from the literature cited above that preparations suitable for stabilizing proteins should have glassy, that is to say amorphous, structures whose glass transition temperature is above the intended storage temperature. The glass transition temperature (Tg) is the temperature at which an amorphous or partially crystalline solid is converted from the glassy state into the fluid or viscous state and vice versa. This involves drastic changes in the viscosity and, associated therewith, in the diffusion coefficient and the kinetic mobility of the biological materials. Physical characteristics such as hardness and modulus of elasticity are changed, as are the thermodynamic functions of volume, enthalpy and entropy. The glass transition temperature of, for example, a sugar-containing composition and its residual water content are physically linked together in such a way that increasing residual amounts of water lead to declining glass transition temperatures and vice versa. It is thus possible to infer from measurement of the glass transition temperature, for example by differential scanning calorimetry (DSC), whether a preparation has a residual water content suitable for stabilization or, as stated above, a drying process is successful or not. Besides determining the glass transition temperature by means of DSC, the presence of amorphous structures can also be proved by means of X-ray diffraction investigations., optical and electron microscopic examinations.

It was therefore desirable to provide fully amorphous ancillary substance structures for biological or pharmaceutically active materials so that the embedded biological materials can also be kept stable at room temperature and over a long period. The ancillary substance structures should have a low residual moisture content which can be adjusted intentionally, and have a glass transition temperature which is as high as possible.

WO 97/15288 describes a process for stabilizing biological materials by means of drying processes without freezing, with which partially amorphous ancillary substance structures are obtained. The drying was carried out as vacuum drying (at slightly elevated temperatures <50° C.), although inhomogeneous products are obtained.

WO 96/32096 describes the production of a homogeneous, dispersible powder, which contains a human protein, carbohydrates and/or amino acids and other ancillary substances, for inhalation by means of spray drying. However, it has emerged that amorphous products are not obtained in any of the examples.

EP 0 682 944 Al describes lyophilisates with pharmaceutically acceptable ancillary substances, consisting of a phase with the protein in amorphous mannitol and a second phase with crystalline alanine. However, these formulations cannot stabilize the biological materials sufficiently well over a lengthy period.

SUMMARY OF THE INVENTION

The present invention is based on the object of developing a mild, flexible, readily reproducible, rapid and economic drying process for embedding biological materials, especially human proteins, and of finding stabilizing matrices suitable for this process. It is intended that it be possible with this process to produce fully amorphous and homogeneous products which allow stabilization of the biological materials over a long period.

The present invention relates to a rapid and readily reproducible process for stabilizing biologically active substances by combining the biologically active substance with a stabilizing mixture and drying the resulting mixture into a dry, amorphous product by means of convection drying. The invention also relates to the amorphous, microscopically homogeneous products which are obtained by this process, are in the form of powders and have a uniform geometric, in particular spherical, shape. The invention furthermore relates to the use of substance mixtures for stabilizing biologically active material, in particular proteins by means of spray drying.

DETAILED DESCRIPTION OF THE INVENTION

The object of the invention, of providing an efficient process for producing amorphous preparations which contain biological materials, is achieved by means of convection drying, in particular by means of spray drying, wherein the air inlet temperature is from about 50 C. to about 300 C. and with the mixtures of at least one zwitterion with polar or apolar radical or a mixture of at least one zwitterion with polar or apolar radical and a carbohydrate. The aforementioned mixtures may also contain ancillary substances such as buffers, surfactants, antioxidants, isotonicizing agents, and preservatives. The invention relates in particular to a process for producing dry, amorphous products which, besides biological material, in particular therapeutically active material, contain substance mixtures for stabilization, which is characterized in that a solution or suspension of biological material and a substance mixture consisting of (a) a carbohydrate and at least one zwitterion with polar or apolar radical or derivatives thereof, and/or (b) at least two zwitterions with polar or apolar radicals or derivatives thereof, and/or (c) at least one zwitterion with polar or apolar radical or a plurality of zwitterions with polar or apolar radicals or derivatives thereof, is produced and dried by means of convection drying with adjustment of a relative moisture content of <70%, preferably <40%, in particular <20%, in the stationary phase at an inlet air temperature of 50–300° C., preferably <200° C. This manner of drying proves to be particularly advantageous in relation to the stability of the biological materials in the formulations and ensures yields >90%.

The zwitterions with polar or apolar radicals which are preferably employed are amino carboxylic acids. The substance mixtures employed of group (a) comprise, preferably, mono-, oligo-, polysaccharides, arginine, aspartic acid, citrulline, glutamic acid, histidine, lysine, acetylphenylalanine ethyl ester, alanine, cysteine, glycine, isoleucine, leucine, methionine, phenylalanine, tryptophan, valine and/or derivatives thereof. The substance mixtures of group (b) comprise, preferably, arginine, aspartic acid, citrulline, glutamic acid, histidine, lysine, acetylphenylalanine ethyl ester, alanine, cysteine, glycine, isoleucine, leucine, mehionine, phenylalanine, tryptophan, valine and/or derivatives thereof. The zwitter of group (c) are preferably employed in the form of their salts. Preferably used are the salts of arginine, aspartic acid, citrulline, glutamic acid, histidine, lysine, acetylphenylalanine ethyl ester, alanine, cysteine, glycine, isoleucine, leucine, methionine, phenylalanine, tryptophan, valine and/or derivatives thereof.

Biologically active materials for the purpose of the invention are one or more substances of the groups of proteins, peptides, glycoproteins, lipoproteins, enzymes, coenzymes, antibodies, antibody fragments, virus constituents, cells and cell constituents, vaccines, DNA, RNA, biological therapeutic and diagnostic agents or derivatives thereof.

It is possible where appropriate to add to the solution or suspension of biological material and the substance mixture of groups (a) and/or (b) and/or (c) conventional ancillary substances from the groups of buffers, surfactants, antioxidants, isotonicizing agents, preservatives.

It is possible by spray drying with the features stated herein to modify carbohydrates, amino acids or derivatives thereof which can be dried with difficulty in such a way that they can be dried, or to mix carbohydrates, amino acids or derivatives thereof with a substance or a substance mixture which increase the Tg so that drying becomes possible and the resulting ancillary substance structure is amorphous and is outstandingly suitable for embedding biological materials. Vacuum drying of comparable formulas results in lower glass transition temperatures.

It has been found that in the case of carbohydrates, especially sugars such as, for example, sucrose, fructose, which indeed form amorphous structures after spraying from aqueous or organic solution into a hot air bed, but have low glass transition temperatures (<20° C.) and therefore result in yields which are extremely economically unfavourable on drying, and have low stability on storage, the latter in particular in relation to the retention of amorphous structures, the Tg is increased so much ($\geq 20°$ C.) by addition of zwitterions or derivatives thereof that they can be dried in good yield, and the amorphous structure of the carbohydrates or of the complete formulation is retained or stabilized.

It has furthermore emerged, surprisingly, that it is possible to obtain an amorphous structure as is necessary for stabilizing biological materials by using carbohydrates such as, for example, mannitol, after the spraying from aqueous or organic solution into a hot air bed, by adding zwitterions or derivatives thereof prior to spray drying. At the same time, good yields are achieved therein. This result is surprising since no amorphous structures are obtained when the process is carried out without addition of zwitterions.

On the other hand, it has been found that even zwitterions or derivatives thereof which, although they can be dried after spraying from aqueous or organic solution into a hot air bed, are not obtained in amorphous form from this, are obtained in a fully amorphous form on addition of carbohydrates or derivatives thereof.

Amorphous structures are also obtained when zwitterions or derivatives thereof which, although they can be dried after spraying from aqueous or organic solution into a hot air bed, are not obtained in a fully amorphous form from this, can be converted by suitable admixtures of one or more zwitterions into a fully amorphous form. To produce the amorphous structure it is unnecessary to choose only combinations of zwitterions with polar radicals and apolar radicals; on the contrary it is also possible to employ combinations of zwitterions with only polar or only apolar radicals.

It has further emerged that one or more zwitterions with polar or apolar radicals or derivatives thereof which, although they can be spray-dried, are not obtained in amorphous form, can be converted by specific adjustment of the pH of the solution or suspension before the convection drying into the amorphous state, preferably by adjusting to a pH of 2.0–8.0, preferable 7.0–7.5. A specific adjustment of the pH of the solution before the spray drying can also be worthwhile in those cases (variants a and b) where, although amorphous structures are obtained, the stability of the protein in the amorphous structure is to be further improved or the amorphous structure of the sprayed products is to be further increased. Such an adjustment of the pH may also be necessary for physiological reasons.

The skilled person is able, by suitable combination of the variants mentioned, to increase significantly further the effects already achieved. The teaching of the patent allows him to select a zwitterion with polar or apolar radical so that the dried substance mixture has a raised glass transition temperature and/or an amorphous structure by comparison with a substance mixture without a corresponding addition.

The products obtained with the process according to the invention are amorphous and microscopically homogeneous powders in a particle size range from 0.0005 mm to 1 mm, preferably from 0.001 mm to 0.1 mm. The process according to the invention allows preferably spherical particles to be obtained in a particle size range which is adjustable and can be reproduced surprisingly well. The resulting products have a glass transition temperature=20° C., preferably 40° C., and a residual moisture content <8% (g/g), preferably <4% (g/g). The amorphous structure is furthermore retained over storage times of at least 12 months. Compared with lyophilisates, the products have an apparent density which is higher by at least a factor of 1.15 (15%) than lyophilisates and, compared with products from freeze or vacuum drying, have significantly lower crystalline contents for the same formulation.

The amorphous products, which preferably contain proteins as biological materials, are produced according to the invention by convection drying, in particular by spray drying or spray granulation, by producing a solution or suspension of the biological material and the substance mixture, and carrying out the convection drying at an inlet air temperature of 50–300° C., preferably <200° C., it having emerged that the relative moisture content in the stationary phase must be adjusted to <70%, preferably <40%, in order to obtain a defined product moisture content of <4%. The process according to the invention thus permits the required residual moisture content in the final products to be adjusted intentionally.

It is possible according to the invention for the convection drying to take place by means of fluidized drying, lift air drying or flight drying. Spray or fluidized bed drying is particularly preferably used according to the invention.

In the spray drying, the material to be dried is sprayed in a manner known per se as solution or suspension through nozzles or by means of a rapidly rotating atomizer disc to give a mist of droplets at the upper end of a wide cylindrical container. The resulting mist of droplets is mixed with hot air or an inert gas, which are passed around the atomizing zone into the dryer. If a solution is atomized under otherwise identical conditions by means of a two-component nozzle or disc, although the particle size distribution of the spray embedding is narrower with disc atomization than with nozzle atomization, it is shifted into the coarser region.

Suitable atomizing devices are swirl pressure nozzles, pneumatic nozzles (two-component/three-component nozzles) or centrifugal atomizers. Although pneumatic nozzles require the greatest energy consumption for atomization per kg of liquid, these nozzles are particularly suitable because of their flexibility, for example for achieving particular particle size ranges or particular particle shapes. The process can also be carried out by means of the use of a three-component nozzle technique. It is possible thereby to atomize two liquids simultaneously.

This makes two variants of the atomization possible:

Variant 1

The two liquids are fed separately and, shortly before the atomization, mixed and then atomized. This variant is preferably used when the mixtures of two components are stable for only a short time in one liquid phase.

Variant 2

The two liquids are fed separately, atomized separately and mixed before entering the nozzle orifice. This variant can be used for two immiscible solutions or where the stability of the components is ensured only in the solid-state.

It was possible to use these specific types of atomization for the invention just as well as classical two-component atomization.

A process according to the invention is optimal with an inlet air temperature in the range between 100° C. and 180° C. Since there is also a risk of decomposition of the spray embedding as the inlet air temperature increases, higher temperatures=200° C. are normally not productive but can certainly be considered for specific applications. It is surprising that the stability of the biological materials in the formulations is very good although the hot air used according to the invention for the drying preferably has a temperature of >100° C.

The spraying of the solution after the drying results in preferentially spherical particles in an adjustable and reproducible particle size range. Spherical shapes with favourable flow properties and a particular particle size range are precisely those particularly advantageous for many types of pharmaceutical application.

The drying times with the process according to the invention are not more than one minute.

It is also possible according to the invention to produce granules by spraying the solution of biological material and substance mixture onto a carrier with a particle size range from 0.010 mm to 10 mm, preferably 0.1 to 1 mm.

It is thus possible with the process according to the invention, by using the stated substance mixtures, to improve crucially the drying of carbohydrate-containing compositions. The formulations according to the invention contain as main component a carbohydrate, preferably sugar, and one or more zwitterions with polar or apolar radicals or derivatives thereof, with the glass transition temperature of the sugar being distinctly increased by this zwitterion addition.

Formulations in which the main component are zwitterions with polar or apolar radicals or derivatives thereof can be converted into stable amorphous forms by addition of carbohydrates.

It is also possible as an alternative to the carbohydrates to use zwitterions with polar or apolar radicals or derivatives thereof or mixtures thereof. These formulations can be composed of at least 2 zwitterions or derivatives thereof with polar radicals, at least 2 zwitterions or derivatives thereof with apolar radicals or of at least one zwitterion with polar and apolar radical.

Amorphous and dry formulations can also be obtained by specific adjustment of the pH of the solution of zwitterions with polar or apolar radicals or derivatives thereof, alone or in combination.

Substance mixtures which can be preferably employed according to the invention consist of at least two substances selected from sucrose, L-arginine, L-phenylalanine, L-aspartic acid, L-isoleucine and derivatives thereof.

Besides the compositions indicated in the examples, the following substance mixtures have also proved particularly suitable as matrix for the formation of sprayed products according to the invention:

Mixture (formula) 1:

Sucrose, L-arginine and L-phenylalanine,

Mixture (formula) 2:

L-Arginine, L-aspartic acid and L-isoleucine,

Mixture (formula) 3:

L-Arginine and L-phenylalanine,

Mixture (formula) 4:

L-Arginine, L-phenylalanine and L-aspartic acid.

The invention also relates to the use of the amorphous products produced according to the invention for producing diagnostic or therapeutic compositions by further processing them where appropriate with conventional ancillary substances and excipients.

EXAMPLE 1

The carbohydrate and the amino acid (AA) were dissolved in water at RT. Adjustment of the pH may be necessary depending on the biological material used. This solution is then spray dried.

It is evident from the following table 1 that, for example, sucrose or fructose cannot be dried in economically good yields because of the low glass transition temperature (1.1 and 1.5), whereas the solutions with AA addition result after the drying as fine-particle dry powders in good yields (1.2 –1.4 and 1.6). It is further evident from the table that carbohydrates such as, for example, mannitol, which after the drying normally do not form amorphous structures and result in economically favourable yields (1.7), on addition of zwitterions or derivatives thereof form an amorphous structure and result in good yields as are necessary for the stabilization of biological materials (1.8).

Carbohydrates with Addition of Zwitterions with Polar/apolar Radicals

TABLE 1

| Example | Carbo-hydrate mg/ml | Amino acid mg/ml | Residual water content % | Glass transition temperature ° C. Crystal structure State of aggregation |
|---|---|---|---|---|
|  | Sucrose | L-Arginine |  |  |
| (1.1) | 275 | 0 | 2.8 | <20° C. X-ray amorphous tacky mass |
| (1.2)* | 100 | 5 | 2.4 | ≧20° C. X-ray amorphous Powder |
|  |  | L-Phenyl-alanine |  |  |
| (1.3) | 100 | 5 | 2.8 | ≧20° C. X-ray amorphous Powder |
| (1.4) | 100 | 20 | 2.5 | ≧20° C. X-ray amorphous Powder |
|  | Fructose |  |  |  |
| (1.5) | 275 | 0 | 2.3 | <20° C. X-ray amorphous tacky mass |
| (1.6) | 100 | 5 | 4.0 | ≧20° C. X-ray amorphous Powder |

TABLE 1-continued

| Example | Carbo-hydrate mg/ml | Amino acid mg/ml | Residual water content % | Glass transition temperature ° C. Crystal structure State of aggregation |
|---|---|---|---|---|
|  | Mannitol | L-Arginine/ L-phenyl-alanine |  |  |
| (1.7) | 55 | 0 | 0.4 | — crystalline powder |
| (1.8)* | 100 | 10/10 | 2.5 | ≧20° C. X-ray amorphous Powder |

*pH adjusted to 7.3 ± 0.2

EXAMPLE 2

The amino acid and the carbohydrate were dissolved in water at RT and spray dried. It is evident from the following table 2 that the pure AA results in a crystalline crystal structure (2.1 and 2.4), but amorphous structures are obtained on addition of carbohydrate (2.2, 2.3, 2.5).

Zwitterions with Polar/apolar Radicals on Addition of Carboyhydrates

TABLE 2

| Example | Amino acid mg/ml | Carbo-hydrate mg/ml | Residual water content % | Glass transition temperature ° C. Crystal structure State of aggregation |
|---|---|---|---|---|
|  | L-Arginine | Methyl-hydroxy-propyl-cellulose 2910 |  |  |
| (2.1) | 55 | 0 | 10.2 | — crystalline powder ≧20° C. |
| (2.2) | 20 | 4 | 7.2 | ≧20° C. X-ray amorphous powder |
|  |  | Sucrose |  |  |
| (2.3) | 20 | 4 | 6.4 | ≧20° C. X-ray amorphous powder |
|  | L-Phenyl-alanine |  |  |  |
| (2.4) | 55 | 0 | 0.4 | — crystalline powder 20° C. |
| (2.5) | 20 | 4 | 4.6 | X-ray amorphous powder |

EXAMPLE 3

The amino acids were dissolved in water at RT and spray dried. It is evident from the following table 3 that the pure AA results in a crystalline structure (3.1–3.4), but amorphous structures are obtained on addition of a second AA (3.5–3.8). In Examples 3.9–3.11, the Tg values of vacuum dryings are indicated. The Tg values on vacuum drying of comparable formulas are distinctly below the values in the process according to the invention.

Zwitterions with Polar/apolar Radicals on Further Addition of Zwitterions with Polar/apolar Radicals

TABLE 3

| Example | Amino acid mg/ml | Amino acid mg/ml | Residual water content % | Glass transition temperature ° C. Crystal structure State of aggregation |
|---|---|---|---|---|
| | L-Arginine | | | |
| (3.1) | 55 | 0 | 10.2 | — crystalline powder |
| | L-Isoleucine | | | |
| (3.2) | 21.7 | 0 | 0.4 | — crystalline powder |
| | L-Phenyl-alanine | | | |
| (3.3) | 55 | 0 | 0.4 | — crystalline powder |
| | L-Aspartic acid | | | |
| (3.4) | 6.7 | 0 | 0.3 | — crystalline powder |
| | L-Phenyl-alanine | L-Isoleucine | | |
| (3.5) | 20 | 4 | 1.2 | ≧20° C. X-ray amorphous powder |
| | L-Arginine | L-Phenyl-alanine | | |
| (3.6) | 20 | 4 | 5.7 | ≧20° C. X-ray amorphous powder |
| | | L-Aspartic acid | | |
| (3.7) | 4 | 20 | 5.5 | ≧20° C. X-ray amorphous powder |
| | | L-Aspartic acid/ L-Isoleucine | | |
| (3.8) | 40 | 22 10 | 4.2 | ≧20° C. X-ray amorphous powder |

Vacuum drying

TABLE 3.1

| Example | Amino acid mg/ml | Amino acid mg/ml | Residual water content % | Glass transition temperature ° C. |
|---|---|---|---|---|
| | L-Arginine | L-Phenyl-alanine | | |
| 3.9 | 33.4 | 7.9 | 9.9 | 1.3 |
| 3.10 | 34.8 | 6.6 | 10.7 | 0.0 |
| 3.11 | 35.8 | 5.6 | 10.0 | 1.3 |

EXAMPLE 4

The amino acid was dissolved in water at RT and spray dried. It is evident from the following table 4 that an X-ray-amorphous structure is formed by specific adjustment of the pH (4.1 and 4.3), otherwise only a crystalline structure is obtained (4.2 and 4.4).

Zwitterions with Polar/apolar Radicals

TABLE 4

| Example | Amino acid mg/ml | Amino acid mg/ml | Residual water content % | Glass transition temperature ° C. Crystal structure State of aggregation |
|---|---|---|---|---|
| | L-Arginine | | | |
| (4.1) | 55 pH 7.2 adjusted with H₃PO₄ | 0 | 5.1 | ≧20° C. X-ray amorphous Powder |
| (4.2) | 55 | 0 | 10.2 | — crystalline powder |
| | L-Aspartic acid | | | |
| (4.3) | 8.3 pH 7.2 adjusted with NaOH | 0 | 0.5 | ≧20° C. X-ray amorphous Powder |
| (4.4) | 6.7 | 0 | 0.3 | — crystalline powder |

EXAMPLE 5

The carbohydrate, the AA and other ancillary substances were dissolved in water at RT, adjusted to pH 7.3±0.2 and spray dried.

The following tables shows optimized active drug formulas according to the process according to the invention (5.2–5.6). A placebo formula (5.1) was used for comparison. No decomposition products were shown by any of the formulas after the drying, it being possible to detect high molecular weight (HMW) aggregates and EPO dimers not exceeding 0.2% in formulas 5.2–5.6. This value is not exceeded even after storage for 3 months (shown by Example 5.3).

By contrast, a formula not according to the invention shows a very high content of high molecular weight (HMW) aggregates and EPO dimers even immediately after the drying (5.7).

TABLE 5

| Example | EPO U/Carbo-hydrate mg/ml | Amino acids/ ancillary substance mg/ml | Residual water content % | Glass transition temperature ° C. Crystal structure State of aggregation |
|---|---|---|---|---|
| | Sucrose | L-Arginine L-Phenyl-alanine/ Tween 20 | | |
| (5.1) | — 100 | 20/20 0.2 | 2.8 | ≧20° C. X-ray amorphous powder |
| | EPO/sucrose | | | |
| (5.2) | 7000/50 | 10/10/— | 3.5 | ≧20° C. X-ray amorphous powder |
| (5.3) | 7010/50 | 10/10/0.1 | 2.4 | ≧20° C. X-ray amorphous powder |
| (5.4) | 14020/100 | 20/20/0.2 | 2.9 | ≧20° C. X-ray amorphous powder |

TABLE 5-continued

| Example | EPO U/Carbo-hydrate mg/ml | Amino acids/ ancillary substance mg/ml | Residual water content % | Glass transition temperature ° C. Crystal structure State of aggregation |
|---|---|---|---|---|
| | EPO/— | L-Arginine/ L-aspartic acid/L-iso-leucine/ Tween 20 | | |
| (5.5) | 5010/— | 30/10/10/0.1 | 4.3 | ≧20° C. X-ray amorphous powder |
| | | L-Arginine/ L-aspartic acid/ L-phenyl-alanine/ Tween 20 | | |
| (5.6) | 5010/— | 30/10/10/0.1 | 4.4 | ≧20° C. X-ray amorphous powder |

Storage stability of Example 5.3 in refrigerator, at RT and 40° C. for 3 months

TABLE 5.1

| 5.3 | HMW aggregates | | | EPO dimers | | |
|---|---|---|---|---|---|---|
| | Fridge (4–6° C.) | RT (20–22° C.) | 40° C. | Fridge (4–6° C.) | RT (20–22° C.) | 40° C. |
| Initial | | <0.1% | | | <0.1% | |
| After 2 months | <0.1% | <0.1% | <0.1% | <0.1% | <0.1% | <0.1% |
| After 3 months | <0.1% | <0.1% | <0.1% | <0.1% | <0.1% | 0.1% |

Content of HMW aggregates and EPO dimers in a formula not according to the invention immediately after drying:

TABLE 5.2

| Example | EPO U/carbohydrate mg/ml | Residual water content % | HMW aggregates % | EPO dimers % |
|---|---|---|---|---|
| | EPO/lactose | | | |
| (5.7) | 7010/50 | 3.4 | 9 | 2 |

EXAMPLE 6

The following Examples 6 to 12 illustrate the effect of the chosen conditions in the process according to the invention on the final products. The following formulas 1 to 4 were investigated:

Mixture (formula) 1:

Sucrose, L-arginine and L-phenylalanine (5:1:1)

Mixture (formula) 2:

L-Arginine, L-aspartic acid and L-isoleucine (3:1:1)

Mixture (formula) 3:

L-Arginine and L-phenylalanine (1:1)

Mixture (formula) 4:

L-Arginine, L-phenylalanine and L-aspartic acid (3:1:1)

Spray drying of substance mixtures 1 to 4:

TABLE 6

| Starting materials | Composition of the solution | | | |
|---|---|---|---|---|
| | Mixture | | | |
| | 1 | 2 | 3 | 4 |
| Sucrose | 50 mg/ml | | | |
| L-Arginine | 10 mg/ml | 30 mg/ml | 20 mg/ml | 30 mg/ml |
| L-Phenyl-alanine | 10 mg/ml | | 20 mg/ml | 10 mg/ml |
| L-Aspartic acid | | 10 mg/ml | | 10 mg/ml |
| L-Isoleucine | | 10 mg/ml | | |

EXAMPLE 7

Spray Drying with Different Inlet Air Temperatures

The four mixtures were spray dried at three different inlet air temperatures, namely at 100° C., 140° C. and 180° C. A very important parameter in the spray drying is the rel. moisture content in the stationary phase of the spray drying. The stationary phase is regarded as being the drying section where the process of drying the sprayed particles is complete and the maximum temperature stress on the dried sprayed particles is reached. The relative moisture content in the stationary phase determines the moisture content of the product after the drying. The relative moisture content to be chosen in this case depends on the composition of the formulation. The relative moisture content in the stationary phase for the four mixtures was chosen according to the invention to be very low at less than 40% (specifically about 10% in this case). This established whether spray drying of mixtures 1–4 is still in fact possible. Spray drying of the four mixtures was possible satisfactorily under the above mentioned conditions. In all cases, fine-powder spray embeddings (SE) were obtained in good yield (>90%). There were no deposits on the tower cone and the pipelines, and discharge of the products was possible satisfactorily despite the low dust/air ratios (<<50 g/m³ (STP)).

Relative Moisture Content 10%

TABLE 7

| Inlet air temperature ° C. | Rel. moisture content, stationary phase % | Water vaporization rate Approx. g/h | Solid (from 7% strength solution) approx. g/h |
|---|---|---|---|
| 60 | 10 | 100 | 7.5 |
| 100 | 10 | 600 | 45.2 |
| 140 | 10 | 1000 | 75.3 |
| 180 | 10 | 1400 | 105.4 |

EXAMPLE 8

Tests on the Spray Embedding Products (SE)

a) pH, Density, Water Content, Osmolality

TABLE 8

| Mixture | Inlet air temperature ° C. | SE water content % | PH Initial solution/SE | Density Initial solution/SE g/cm³ | Osmolality Initial solution/SE mOsm/kg |
|---|---|---|---|---|---|
| Mixture 1 | 100 | 3.2 | 7.4/7.44 | 1.025/1.023 | 270/272 |
| Mixture 1 | 140 | 3.0 | 7.4/7.44 | 1.025/1.022 | 270/270 |
| Mixture 1 | 180 | 3.0 | 7.4/7.43 | 1.025/1.020 | 270/273 |
| Mixture 2 | 100 | 3.9 | 7.4/7.44 | 1.017/1.021 | 292/270 |
| Mixture 2 | 180 | 2.6 | 7.4/7.44 | 1.017/1.022 | 292/279 |
| Mixture 3 | 100 | 2.4 | 7.4/7.43 | 1.013/1.010 | 216/213 |
| Mixture 3 | 180 | 2.7 | 7.4/7.43 | 1.013/1.011 | 216/212 |
| Mixture 4 | 100 | 3.6 | 7.4/7.38 | 1.018/1.023 | 274/254 |
| Mixture 4 | 180 | 2.7 | 7.4/7.37 | 1.018/1.023 | 274/254 |

The spray embedding dissolved in water gave identical values for the pH, the density and the osmolality as for the initial solution. The water content of the spray embeddings decreased slightly as the inlet air temperature increased, although the rel. moisture content in the stationary phase was kept constant. In particular, mixture 1 showed an almost contant water content at all inlet air temperatures.

b) Crystal Structure

Irrespective of the inlet air temperatures, all the spray embeddings are X-ray amorphous by comparison with the initial mixture.

c) Electron Microghraphs

The electron micrographs of the spray embeddings from mixture 1 shows that the SE particles are in the form of almost ideal complete spheres, with the surface changing from a texture resembling a golf ball to a smooth appearance with increasing inlet air temperature. To demonstrate that complete spheres are present,the spray embeddings were ground. The completely spherical shape can be deduced unambiguously from the fragments. The mode of atomization, nozzle or disc atomization, has no effect whatsoever on the shape of the SE particles.

d) Particle size distribution

Mixture 1 was used to demonstrate that the particle size distribution remains approximately constant at different spraying rates.

TABLE 8.1

| Inlet air temperature ° C. | Rel. moisture content, stationary phase % | Spraying rate g/h | Particle size d10/d50/d90 μm | Particle size RRSB-d' μm |
|---|---|---|---|---|
| 100 | 10 | 640.0 | 0.8/3.7/9.7 | 5.7 |
| 140 | 10 | 1035.0 | 0.6/5.3/12.6 | 6.6 |
| 180 | 10 | 1455.0 | 0.7/4.0/11.9 | 6.3 |

It was also established that virtually identical particle size distributions are obtained with the same inlet air temperature and approximately the same spraying rate.

TABLE 8.2

| Inlet air temperature ° C. | Rel. moisture content, stationary phase % | Spraying rate G/h | Particle size d10/d50/d90 μm | Particle size RRSB-d' μm |
|---|---|---|---|---|
| 100 | 10 | 566.0 | 0.7/4.0/10.5 | 5.8 |
| 100 | 10 | 640.0 | 0.8/3.7/9.7 | 5.7 |
| 140 | 10 | 1067.5 | 0.8/4.0/11.6 | 6.2 |
| 140 | 10 | 1035.0 | 0.6/5.3/12.6 | 6.6 |

EXAMPLE 9

Measurement of the Glass Transition Temperature (Tg) by Differential Scanning Calorimetry (DSC)

To determine the glass transitions of the dried samples, and the crystallization and melting peaks, a DSC 7 apparatus from Perkin-Elmer (Überlingen) with CCA 7 low-temperature control with liquid nitrogen (Messer, Griesheim) and a TAC 7/DX signal transducer was used. The weights of the samples were between 5 and 20 mg, weighed into aluminium crucibles (Perkin-Elmer) previously weighed using an autobalance AD4 microbalance (Perkin-Elmer). The crucibles were then tightly closed with a lid (Cover, Perkin-Elmer) using a universal closure press (Perkin-Elmer), placed in the measurement cell flushed with nitrogen and measured at a heating rate of 10° C./min.

The Tg of mixture 1 were determined by means of DSC. With a water content <4%, the respective Tg were advantageously far above room temperature, which means that the mixtures are very suitable for stabilizing biological material, in particular human proteins.

TABLE 9

| Inlet air temperature ° C. | SE water content % | Tg ° C. |
|---|---|---|
| 100 | 3.2 | 57.6 |
| 140 | 3.0 | 58.8 |
| 100 | 3.8 | 57.0 |
| 140 | 7.5 | 28.2 |

EXAMPLE 10

Differing Rel. Moisture Content in the Stationary State

It is shown with mixture 1 how far the rel. moisture content of the stationary phase influences, with conditions which are otherwise constant, the product moisture content and thus the Tg.

TABLE 10

| Inlet air temperature ° C. | Rel. moisture content, stationary phase % | Water content % | Tg ° C. |
|---|---|---|---|
| 140 | 4 | 1.5 | 67.7 |
| 140 | 10 | 3.0 | 58.8 |
| 140 | 25 | 5.9 | 31.7 |
| 140 | 33 | 6.5 | 29.1 |
| 140 | 36 | 7.5 | 28.2 |

EXAMPLE 11

Effect of the Initial Concentration of the Solution on the Spray Embedding

An increase in the initial concentration of the solution is possible in principle up to the solubility limits determined by the ancillary substances and results in almost the same physical properties of the spray embeddings as from a 7% strength solution. This is illustrated by the following table based on mixture 1.

TABLE 11

| Inlet air temperature °C. | Concentration of the solution % | Tg/water content pH °C./% | Particle size d10/d50/d90 µm | Particle size RRSB-d' µm |
|---|---|---|---|---|
| 100 | 15 | 57.3/3.6/7.5 | 0.8/4.6/12.9 | 6.7 |
| 100 | 15 | 52.8/3.4/7.44 | 0.7/4.6/10.8 | 6.0 |
| 100 | 7 | 57.6/3.2/7.38 | 0.8/3.7/9.7 | 5.7 |

EXAMPLE 12 a) Testing of various atomization units (two-component nozzle, atomizer disc) using mixture 1

The use of different atomization units has effects on the particle size distributions of the spray embeddings.

TABLE 12

| Inlet air temperature °C. | Atomization unit µm | Atomization pressure or speed of rotation Bar/rpm | Particle size d10/d50/d90 µm | Particle size RRSB-d' µm | Gradient of the line in the RRSB grid l |
|---|---|---|---|---|---|
| 100 | two-comp. nozzle | 3 bar | 0.8/3.7/9.7 | 5.7 | 1.018 |
| 140 | two-comp. nozzle | 3 bar | 0.6/5.3/12.6 | 6.6 | 1.052 |
| 180 | two-comp. nozzle | 3 bar | 0.7/4.0/11.9 | 6.3 | 0.994 |
| 100 | disc | max. | 1.7/11.9/23.3 | 15.3 | 1.238 |

Disc atomization is unsuitable for pulmonary uses of the SE products, which require particle sizes <10 µm. In addition, the flexibility of the two-component nozzle is considerably greater than that of a disc for shifting particle size ranges. A disadvantage is that on sterile operation with two-component atomization it is necessary for the atomization medium to be sterilized by filtration. The other physical parameters of the SE products do not depend on the mode of atomization, appearance included. Atomization media which can be employed are the known media such as compressed air or inert gases such as, for example, noble gases (neon, argon etc.) or carbon dioxide.

b) Different Nozzle Combinations

The specific nozzle combinations (three-component nozzles) are used for feeding and atomizing two liquids simultaneously.

The spray embeddings obtained with both variants of the three-component nozzle had physical parameters agreeing with those of the spray embeddings obtained from the two-component atomization. Even the Tg and the X-ray-amorphous form were identical.

EXAMPLE 13

Reproducibility With Identical/different Batch Sizes

The process is reproducible with identical or different batch sizes as shown by the example of mixture 1. The. SE products obtained in all cases have physical parameters of the spray embeddings which are within very narrow limits. It is thus possible to apply the results of the trial batches directly to larger batches, and hence a process ready for production is available.

TABLE 13

| Inlet air temperature °C. | Batch size Items | Crystal structure | Particle size d10/d50/d90 µm | Particle size RRSB-d' µm | DSC Tg/water content °C./% |
|---|---|---|---|---|---|
| 100 | 1000 | X-ray amorphous | 0.8/3.7/9.7 | 5.7 | 57.6/3.2 |
| 140 | 1000 | X-ray amorphous | 0.6/5.3/12.6 | 6.6 | 58.8/3.0 |
| 180 | 1000 | X-ray amorphous | 0.7/4.0/11.9 | 6.3 | 57.0/3.0 |
| 140 | 2000 | X-ray amorphous | 0.8/4.0/11.6 | 6.2 | 58.8/2.8 |
| 100 | 300 | X-ray amorphous | /.7/4.0/10.5 | 5.8 | 57.0/3.2 |

What is claimed is:

1. A method of producing dry, amorphous, and stabilized biological material comprising:

a) dissolving at least one carbohydrate and at least one amino carboxylic acid into water;

b) suspending a biological material into the mixture from step (a);

c) adjusting the pH of the solution of step (b) to from about 7.0 to about 8.0; and d) convection drying the solution of step (c) at a temperature from about 100° C. to about 180° C. to a residual moisture content of less than about 8 percent using a method selected from the group consisting of spray-drying, fluidized bed drying, lift air drying and flight drying, thereby producing the dry, amorphous and stabilized biological material having a glass transition temperature of greater than about 20° C.

2. The method of claim 1 wherein the dry, amorphous and stabilized a biological material obtained has a glass transition temperature of greater than about 40° C. and a residual moisture content of less than about 4 percent.

3. The method of claim 1 wherein the dry, amorphous and stabilized biological material obtained are in the form of powders and have particle size range from about 0.0005 mm to about 1.0 mm.

4. The method of claim 3 wherein the dry, amorphous and stabilized biological material obtained are in the form of powders and have particle size range from about 0.001 mm to about 0.1 mm.

5. A method of producing dry, amorphous, and stabilized biological material comprising:

a) dissolving at least one amino carboxylic acid into water;

b) suspending a biological material into the solution from step (a);

c) adjusting the pH of the solution of step (b) to from about 7.0 to about 8.0; and d) convection drying the solution of step (c) at a temperature from about 100° C. to about 180° C. using a method selected from the group consisting of spray-drying, fluidized bed drying, lift air drying and flight drying, thereby producing the dry, amorphous and stabilized biological material with a glass transition temperature of greater than or equal to 20° C. and a residual moisture content of less than about 8 percent.

6. The method of claim 5 wherein the dry, amorphous and stabilized biological material obtained has a glass transition temperature of greater than about 40° C. and a residual moisture content of less than about 4 percent.

7. The method of claim 5 wherein the dry, amorphous and stabilized biological material obtained are in the form of powders and have particle size range from about 0.0005 mm to about 1.0 mm.

8. The method of claim 7 wherein the dry, amorphous and stabilized biological material obtained are in the form of powders and have particle size range from about 0.001 mm to about 0.1 mm.

* * * * *